United States Patent [19]
Zhang et al.

[11] Patent Number: 6,140,488
[45] Date of Patent: Oct. 31, 2000

[54] RAS-BINDING PROTEIN (PRE1)

[76] Inventors: Xian-feng Zhang, 249 Pearl St., Cambridge, Mass. 02141; Joseph Avruch, 277 St. Paul St., Brookline, Mass. 02445

[21] Appl. No.: 08/942,572

[22] Filed: Oct. 1, 1997

[51] Int. Cl.[7] ........................... C07H 21/04; C12P 21/02; C12N 15/00
[52] U.S. Cl. ................... 536/23.5; 435/69.1; 435/320.1; 530/324; 530/350
[58] Field of Search ........................ 536/23.5; 435/7.23, 435/69.1, 320.1; 530/324, 350

[56] References Cited

PUBLICATIONS

Sambrook et al. "Molecular Cloning: A Laboratory Manual" Second Ed., Cold Spring Harbor Laboratory Press, p. 11.12 to 11.13, 1989.
Current Protocols in Molecular Biology. Massachusetts General Hospital, Harvard Medical School, p. 6.4.5, 1990.
The ATCC Cell Lines and Hybridomas Catalog. 8th edition. American Type Culture Collection. p. 429, 1994.
Afar et al., "Regulation of the Oncogenic Activity of BCR–ABL by a Tightly Bound Substrate Protein R1N1", Immunity, 6:773–782, 1997.
Ahmed et al., "Human brain n–chimaerin cDNA encodes a novel phorbol ester receptor", Biochem. J., 272:767–773, 1990.
Ahmed et al., "The *Caenorhabditis elegans* unc–13 gene product is a phospholipid–dependent high–affinity phorbol ester receptor", Biochem. J., 27:995–999, 1992.
Avruch et al., "Raf meets Ras: completing the framework of a signal transduction pathway", Trends in Biochem., 19:279–283, 1994.
Bos, Johannes L., "ras Oncogenes in Human Cancer: A Review", Cancer Res., 49:4682–4689, 1989.
Cahill et al., "Signalling pathways: Jack of all cascades", Cur. Biol., 6(1):16–19, 1996.
Cowley et al., "Activation of MAP Kinase Kinase Is Necessary and Sufficient for PC12 Differentiation and for Transformation of NIH 3T3 Cells", Cell, 77:841–852, 1994.
D'Arcangelo et al., "A Branched Signaling Pathway for Nerve Growth Factor Is Revealed by Src–, Ras–, and Raf–Mediated Gene Inductions", Mole. and Cell. Biol., 13:3146–3155, 1993.
Dickson et al., "Genetics of signal transduction in invertebrates", Cur. Opin. Genet. Dev., 4:67–70, 1994.
Fanti et al., "Signalling by Receptor Tyrosine Kinases", Annu. Rev. Biochem., 62:453–481, 1993.
Farrar et al., "Activation of the Raf–1 kinase cascade by coumermycin–induced dimerization", Nature, 383:178–181, 1996.
Katz et al., "Signal transduction from multiple Ras effectors", Cur. Opin. Genet. & Dev., 7:75–79, 1997.
Khosravi–Far et al., "Activation of Rac1, RhoA, and Mitogen–Activated Protein Kinases Is Required for Ras Transformation", Mol. Cell. Biol., 15:6443–6453, 1995.

Kuroda et al., "Different Effects of Various Phospholipids on Ki–Ras–, Ha–Ras–, and Rap1B–induced B–Raf Activation", J. Biol. Chem., 271:14680–14683, 1996.
Leevers et al., Requirement for Ras in Raf activation is overcome by targeting Raf to the plasma membrane, Nature, 369:411–414, 1994.
Luo et al., "Oligomerization activates c–Raf–1 through a Ras–dependent mechanism", Nature, 383:181–185, 1996.
Marshall, Christopher J., "Ras effectors", Cur. Opin. Cell Biol., 8:197–204, 1996.
McCollam et al., "Functional Roles for the Pleckstrin and Dbl Homology Regions in the Ras Exchange Factor Son–of– sevenless", J. Biol. Chem., 270:15954–15957, 1995.
Mineo et al., "Physical Association with Ras Enhances Activation of Membrane–bound raf (RafCAAX)*", J. Biol. Chem., 272:10345–10348, 1996.
Mizushima et al., "pEF–BOS, a powerful mammalian expression vector", Nucl. Acids Res., 18:5322, 1990.
Oldman et al., "Activation of the Raf–1/MAP kinase cascade is not sufficient for Ras transformation of RIE–1 epithelial cells", Proc. Natl. Acad. Sci. USA, 93:6924–6928, 1996.
Ono et al., "Phorbol ester binding to protein kinase C requires a cysteine–rich zinc–finger–like sequence", Proc. Natl. Acad. Sci. USA, 86:4868–4871, 1989.
Ponting et al., "A novel family of Ras–binding domains", Trends in Biochem. Sci., 21:422–425, 1996.
Qiu et al., "An essential role for Rac in Ras transformation", Nature, 374:457–459, 1995.
Ramocki et al., "Signaling through Mitogen–Activated Protein Kinase and Rac/Rho Does Not Duplicate the Effects of Activated Ras on Skeletal Myogenesis", Mol. Cell. Biol., 17:3547–3555, 1997.
Rapp et al., "raf Family Serine/Threonine Protein Kinases in Mitogen Signal Transduction", Cold Spring Harb. Symp. Quant. Biol., LIII:173–184, 1988.
Ren et al., "Identification of a Ten–Amino Acid Proline–Rich SH3 Binding Site", Science, 259:1157–1161, 1993.
Rodriguez–Viciana et al., "Role of Phosphoinositide 3–OH Kinase in Cell Transformation and Control of the Actin Cytoskeleton by Ras", Cell, 89:457–467, 1997.
Sakane et al., "Porcine diacylglycerol kinase sequence has zinc finger and E–F hand motifs", Nature, 344:345–348, 1990.

(List continued on next page.)

*Primary Examiner*—Yvonne Eyler
*Assistant Examiner*—Brenda G. Brumback
*Attorney, Agent, or Firm*—Fish & Richardson P.C.

[57] ABSTRACT

Disclosed is a Ras-binding protein designated PRE1. PRE1 occurs naturally in various mammalian tissues and cell types. An isolated DNA encoding PRE1, vectors and cells containing the DNA, and PRE1-specific antibodies are also disclosed. Also disclosed is an in vitro screening method for identifying a substance which modulates PRE1-Ras binding, and an in vitro method for identifying a substance that modulates PRE1 gene expression.

8 Claims, 2 Drawing Sheets

OTHER PUBLICATIONS

Stokoe et al., "Activation of Raf as a Result of Recruitment to the Plasma Membrane", Science, 264:1463–1467, 1994.

Stokoe et al., "Activation of c–Raf–1 by Ras and Src through different mechansims: activation in vivo and in vitro", EMBO J., 16:2384–2396, 1997.

Taylor et al., "Cell cycle–dependent activation of Ras", Cur. Biol., 6(12):1621–1627, 1996.

Valencia et al., "The ras Protein Family: Evolutionary Tree and Role of Conserved Amino Acids", Biochem., 30:4637–4648, 1991.

van Corven et al., "Pertussis toxin–sensitive activation of $p21^{ras}$ by G protein–coupled receptor agonists in fibroblasts", Proc. Natl. Acad. Sci. USA, 90:1257–1261, 1993.

Whitehead et al., "Dbl family proteins", Biochimica et Biophysica Acta, 1332:F1–F23, 1997.

Wittinhofer et al., "How Ras–related proteins talk to their effectors", Trends in Biochem. Sci., 21:488–491, 1996.

Woodrow et al., "$p21^{ras}$ Function Is Important for T Cell Antigen Receptor and Protein Kinase C Regulation of Nuclear Factor of Activated T Cells", J. of Immun., 150:3853–3861, 1993.

Zhang et al., "Normal and oncogenic $p21^{ras}$ proteins bind to the amino–terminal regulatory domain of c–Raf–1", Nature, 364:308–313, 1993.

Zhang et al., "Kinase Suppressor of Ras Is Ceramide–aCtivated Protein Kinase", Cell, 89:63–72, 1997.

Slepnev et al., NCBI Sequence Submission, Accession No. AF002251, May 5, 1997.

```
GTAGCTGCGCCGCTGACTGAGGCCTTGGCCATGGCTTCCCCGGCCATCGGGCAACGTCCC      60
                             M  A  S  P  A  I  G  Q  R  P
TACCCGCTGCTCCTAgATCCCGAGCCGCCGCGGTATCTGCAGAGTCTGGGTGGCACCGAG    120
 Y  P  L  L  L  D  P  E  P  P  R  Y  L  Q  S  L  G  G  T  E
CCGCCACCTCCCGCCCGGCCGCGCCGCTGCATCCCCACGGCCCTGATCCCCGCGGCCGGG    180
 P  P  P  P  A  R  P  R  R  C  I  P  T  A  L  I  P  A  A  G
GCGTCAGAGGATCGCGGTGGCAGGAGGAGTGGCCGGAGGGACCCCGAACCCACGCCCCGA    240
 A  S  E  D  R  G  G  R  R  S  G  R  R  D  P  E  P  T  P  R
GACTGCCGACACGCTCGCCCTGTCCGGCCCGGTCTGCAGCCGAGACTGCGGCTGCGACCT    300
 D  C  R  H  A  R  P  V  R  P  G  L  Q  P  R  L  R  L  R  P
GGGTCACACCGACCCCGCGACGTGAGGAGCATCTTCGAGCAGCCGCAGGATCCCCGCGTC    360
 G  S  H  R  P  R  D  V  R  S  I  F  E  Q  P  Q  D  P  R  V
TTGGCCGAGAGAGGCGAGGGGCACCGTTTCGTGGAACTGGCGCTGCGGGGCGGTCCGGGC    420
 L  A  E  R  G  E  G  H  R  F  V  E  L  A  L  R  G  G  P  G
TGGTGTGACCTGTGCGGACGAGAGGTGCTGCGGCAGGCGCTGCGCTGCGCTAATTGTAAA    480
 W  C  D  L  C  G  R  E  V  L  R  Q  A  L  R  C  A  N  C  K
TTCACCTGCCACTCGGAGTGCCGCAGCCTGATCCAGTTGGACTGCAGACAGAAGGGGGGC    540
 F  T  C  H  S  E  C  R  S  L  I  Q  L  D  C  R  Q  K  G  G
CCTGCCCTGGATAGACGCTCTCCAGGAAGCACCCTCACCCCAACCTTGAACCAGAATGTC    600
 P  A  L  D  R  R  S  P  G  S  T  L  T  P  T  L  N  Q  N  V
TGTAAGGCAGTGGAGGAGACACAGCACCCGCCCACGATACAGGAGATCAAGCAGAAGATT    660
 C  K  A  V  E  E  T  Q  H  P  P  T  I  Q  E  I  K  Q  K  I
GACAGCTATAACAGCAGGGAGAAGCACTGCCTGGGCATGAAGCTGAGTGAAGATGGCACC    720
 D  S  Y  N  S  R  E  K  H  C  L  G  M  K  L  S  E  D  G  T
TACACAGGTTTCATCAAAGTGCATTTGAAGCTCCGACGGCCAGTGACGGTGCCCGCTGGA    780
 Y  T  G  F  I  K  V  H  L  K  L  R  R  P  V  T  V  P  A  G
TCCGGCCCCAGTCCATCTATGGATGCCATTAAGGAAGTGAACCCTGCAGCCACCACAGAC    840
 S  G  P  S  P  S  M  D  A  I  K  E  V  N  P  A  A  T  T  D
AAGCGGACTTCCTTCTACCTGCCACTCGATGCCATCAAGCAGCTACATATCAGCAGCACC    900
 K  R  T  S  F  Y  L  P  L  D  A  I  K  Q  L  H  I  S  S  T
ACCACGGTTAGTGAGGTCATCCAGGGGCTGCTCAAGAAGTTCATGGTTGTGGACAACCCA    960
 T  T  V  S  E  V  I  Q  G  L  L  K  K  F  M  V  V  D  N  P
CAGAAGTTTGCACTTTTTAAGCGGATACACAAAGATGGACAAGTGCTCTTCCAGAAACTC   1020
 Q  K  F  A  L  F  K  R  I  H  K  D  G  Q  V  L  F  Q  K  L
TCCATTGCTGACTATCCTCTCTACCTTCGTCTGCTCGCTGGGCCTGACACCGATGTTCTC   1080
 S  I  A  D  Y  P  L  Y  L  R  L  L  A  G  P  D  T  D  V  L
AGCTTTGTGCTAAAGGAGAATGAAACTGGAGAGGTGGAGTGGGATGCCTTTTCCATTCCT   1140
 S  F  V  L  K  E  N  E  T  G  E  V  E  W  D  A  F  S  I  P
GAACTCCAGAACTTTTTAACTATCCTGGAAAAAGAGGAGCAGGACAAGATCCATCAACTG   1200
 E  L  Q  N  F  L  T  I  L  E  K  E  E  Q  D  K  I  H  Q  L
CAAAAGAAGTACAACAAATTCCGTCAGAAACTGGAAGAGGCATTACGAGAGTCCCAAGGG   1260
 Q  K  K  Y  N  K  F  R  Q  K  L  E  E  A  L  R  E  S  Q  G
AAGCCGGGGTAACCAGCCGACTTCCTGTCCTCTCAGTGCCCTCCAATTTATTTTATTGTT   1320
 K  P  G  *
```

FIG. 1A

```
AATTATTTTGCAACAAAGAGTTACTGTTAAGACACCTCTGGTGGTTCCACCAGTCGCCTG      1380
CCCAGCAGTTAACAGATGTGGCACAAAGTCTCTTCCACGCAGTGTCTATGCAGGGTTCCG      1440
ATTCCTGCTAACCCACCACACCATGGCTCTGGAGAGCTTCCCGCCTGGGATCAGAACTCC      1500
TGTGGAATGACCAGTGTTTCCCTGCTCAGTCTGCTGGCCTCTCAGAAACCAAATAGTTGC     1560
CTCTCTGGTCACCAAACTCCAATCAATCACCAGCCGGCAAAAGGAAAGAAAGGTTTCAGA     1620
GCCTGTGTGTTCTTTCTCTGGATTTACTCTTCAGTTCCTCTTTTGGTTTGTTTGGTTGGT     1680
TTTTTTTGGCCACGTATAGTATATTTAAGGATCAAATGTGGCATATTCATTCTAGCTAAG     1740
TCCTTGAAAGCAGGAAAATGCTCATGAAAGGACTGTCCTTGCCCCAAGGTGCCTCTTCTT     1800
CTCTAGTACTAGACACTCAGGGTCAGCCTGAGATTTCAAGAGGCTACAGCCTGACCAGGC     1860
CGTCTTCTTATTACCCAGCAGGCTGTGTGCATGCAAACCCAAAGACATATATGCACATCT     1920
GTGTGGTATTTCAGCATGTCTCTGTCCAATGTTTGATATGTTAACATTTGAATTTAATGC     1980
TGTCCTCCTTATGGGTTTCTACCAAAGAGAAACCAGCCACTTATCAATTTTAGTTTCTTG     2040
CTGAGCTGCCAGAAAGTATTACAGAGAAGCACATCCAAGCTGTCTGTGGCCTACGCCTGC     2100
AGGGGTGGGGGCCTGAATCTCCTTGGCCTTCAGTTCCACCTCCACCTCTGGCTTTAGG      2160
GTCTCCAGCTGTTGCCTGAGTAGTAGCTTTGATTACAGCGGTAAAGTCCTCCAACTTGGA    2220
GTCCTTTCTGGTGGAAGCATGGTCTGCTCGCAGCACAGCACTGAGCAGACCCGTGGGCC     2280
TGACTTCCCTGGTGACTTCAGTGCCTTTTTGTTTGCAGAGAAAAGAGTGGGCACTTTGC     2340
TTGAAGCTCTCTGCTGGCTTGCCCCTGGCAGGAAGTGGACAATGGTGCTATAGAGCCAAG    2400
GACACAGCCTCAGAGCACAGGGTGATTGATGATCAGCCTCTTTCCCATCAAGCTTCCCGG    2460
TCAGGCTTTGACTTTGAAGATGCGAGGTTACTAGACTGCATTGACAGCATCAGATTATGA    2520
CTCCAACTCTTGAGTAGTTCAGACTTAAAACCAATCAGCCAGAGTAGCCAGGACTGCAAA    2580
GACACTCAATACAGATGGAGAAAAACTTGTCCCTTTAAAAGAGGGCCAGTGTTTCAATTG    2640
AGCCTCCAGAGGAGACCACTTTCATGTTGTGCTTGCCTTTCCATACCCTTTCCTCGGGTT    2700
GTTTTAAGCCCAAGCTTCTCCGTGTAGCCTAAAAAGTTCCCTACCAGCCCAGCTGAAGCC    2760
ACACTGCTCCCGTCCCAGAAGAACGCCAAATCCTTGTCATTCAAACTGTGCATCGTTTGC    2820
AGAGCTGCAAAAAGCAACATGAGCTAGCGACTCTGAGGTTGTGCACGCCATCAGCCCCTT   2880
GGCTGCCTGAGGTCTCATGCCCAGCCTTACACCTCTCTCCCTTAAGAAGCCCCGTCCTG    2940
CTGTGTACTACAGGGGCACGTGGAATCATTCCCTTCATCCTGCATGTCTGTAGCGTTAGG   3000
AGAAGGCATGGCTCCTGC            3018
```

FIG. 1B

RAS-BINDING PROTEIN (PRE1)

FIELD OF THE INVENTION

The invention relates to recombinant DNA, cell biology and oncology.

BACKGROUND OF THE INVENTION

In humans, mutations in the cellular Ras gene (c-ras) which render Ras constitutively active, have been associated with different types of cancers (Bos et al., *Cancer Res.* 94:4682–4689). Ras relays signals from receptor tyrosine kinases, (Fantl et al., 1993, *Annu. Rev. Biochem.*, 62:453–481), non-tyrosine kinase receptors (Woodrow et al., 1993, *J. Immunol.*, 150: 3853–3861) and heterotrimeric G protein-coupled receptors (Van Corven et al., 1993, *Proc. Nat'l. Acad. Sci.,* 90:1257–1261). Ras is located at the inner surface of the plasma membrane. Activation of cell surface receptors promotes the exchange of Ras-bound GDP for GTP, thereby causing a conformational change in Ras. This conformational change activates Ras so that it interacts with downstream targets or effectors (Wittinghofer et al., 1996, *Trends In Biochem. Sci.,* 21:488–491.

Several candidate Ras effectors have been proposed based on their ability to bind to Ras through its effector loop. Among these are: Raf, PI-3 kinase, members of the Ral-GDS family, Rin-1, AF-6, diacylglycerol kinases, PKC ζ, and MEKK1 (See, e.g., Katz et al., 1997, *Curr. Opin. Genet. Dev.,* 7:75–79; Marshall, 1996, *Curr. Opin. Cell Biol.,* 8:197–204). Activation of effectors such as these leads to activation of other downstream signal transduction molecules. This signaling cascade culminates in the modulation of gene expression, and thereby causes changes in cellular function, growth, and division.

SUMMARY OF THE INVENTION

A Ras effector protein, designated PRE1, has been identified and characterized. PRE1 protein is expressed in various tissues and cell lines, and PRE1 binds to Ras.

The invention features an isolated DNA containing a nucleotide sequence that encodes a PRE1 protein. The PRE1 protein encoded by the DNA shares at least 80% sequence identity with SEQ ID NO:2, and it binds to Ras. The nucleotide sequence can define a DNA molecule whose complement hybridizes under high stringency conditions to a DNA whose nucleotide consists of SEQ ID NO:1. Preferably, the isolated DNA encodes a naturally-occuring mammalian PRE1. In some embodiments, the DNA encodes an amino acid sequence consisting of SEQ ID NO:2. The DNA can contain the nucleotide sequence of SEQ ID NO:1 or the coding region of the nucleotide sequence of SEQ ID NO:1, or degenerate variants of those sequences. The invention also includes a vector containing the above-described DNA, which DNA can be operably linked to one or more expression control sequences. The invention also includes a cell containing such a vector.

The invention features a substantially pure PRE1 protein that includes an amino acid sequence that shares at least 80% sequence identity with SEQ ID NO:2 and binds to Ras. Preferably, the sequence identity is at least 85%, more preferably, it is at least 90%, and most preferably, it is at least 95%. The amino acid sequence of the PRE1 protein can differ from SEQ ID NO:2 solely by conservative amino acid substitutions (i.e., substitution of one amino for another of the same class) or by non-conservative sustitutions, deletions, or insertions located at positions that do not destroy the function of the protein. In some embodiments, the protein has an amino acid sequence consisting of SEQ ID NO:2. Also included in the invention is any naturally-occurring homolog or isoform of SEQ ID NO:2. The invention includes Ras-binding domain-containing PRE1 protein fragments, e.g., amino acids 266–360 or 188–413, and heterologous fusion proteins containing a Ras-binding domain-containing PRE1 protein fragment.

The invention also features a PRE1-specific antibody, which can be polyclonal or monoclonal. The antibody can be conjugated to a detectable label.

The invention also features a screening method for identifying a substance that modulates binding of PRE1 protein to Ras. The method includes the following steps: (a) providing a sample solution of PRE1 protein; (b) adding to the sample solution a candidate substance; (c) adding to the sample solution a Ras sample; and (d) detecting an increase or decrease in binding of PRE1 protein to Ras in the presence of the candidate substance, compared to the binding of PRE1 to Ras in the absence of the candidate substance.

The invention also features a method of producing PRE1 protein. The method includes the following steps: (a) providing a cell transformed with an isolated DNA comprising a nucleotide sequence that encodes a protein the amino acid sequence of which is SEQ ID NO:2; (b) culturing the cell; and (c) collecting the protein encoded by the nucleotide sequence.

The invention also features a screening method for identifying a substance that modulates PRE1 gene expression. The method includes the following steps: (a) providing a test cell; (b) contacting the test cell with a candidate substance; and (c) detecting an increase or decrease in the level of PRE1 gene expression in the presence of the candidate substance, compared to the level of PRE1 gene expression in the absence of the candidate substance.

The invention also features a method for isolating a PRE1-binding substance, e.g., Ras protein. The method includes the following steps: (a) providing a sample of immobilized PRE1 protein; (b) contacting a mixture containing the substance with said immobilized PRE1 protein; (c) separating unbound components of the mixture from bound components of the mixture; (d) recovering the PRE1-binding substance from said immobilized PRE1 protein.

As used herein, "high stringency conditions" means the following: hybridization at 42° C. in the presence of 50% formamide; a first wash at 65° C. with about 2×SSC containing 1% SDS; followed by a second wash at 65° C. with 0.1×SSC.

As used herein, "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Also included is a recombinant DNA that includes a portion of SEQ ID NO:1 and that encodes an alternative splice variant of PRE1.

As used herein, "operably linked" means incorporated into a genetic construct so that expression control sequences effectively control expression of a gene of interest.

As used herein, "protein" means any peptide-linked chain of amino acids, regardless of length or post-translational modification, e.g., glycosylation or phosphorylation.

As used herein, "PRE1" means: (1) a protein, the amino acid sequence of which is SEQ ID NO:2, or (2) a protein that shares at least 80% amino acid sequence identity with SEQ ID NO:2 and binds to Ras.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, "PRE1-specific antibody" means an antibody that binds to a protein, the amino acid sequence of which is SEQ ID NO:2 and displays no substantial binding to other naturally-occuring proteins other than those sharing the same antigenic determinants as PRE1. The term includes polyclonal and monoclonal antibodies.

As used herein, "substantially pure protein" means a protein separated from components that naturally accompany it. Typically, the protein is substantially pure when it is at least 60%, by weight, free from the proteins and other naturally-occurring organic molecules with which it is naturally associated. Preferably, the purity of the preparation is at least 75%, more preferably at least 90%, and most preferably at least 99%, by weight. A substantially pure PRE1 protein can be obtained, for example, by extraction from a natural source, by expression of a recombinant nucleic acid encoding an PRE1 polypeptide, or by chemical synthesis. Purity can be measured by any appropriate method, e.g., column chromatography, polyacrylamide gel electrophoresis, or HPLC analysis. A chemically-synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in $E.\ coli$ or other prokaryotes.

As used herein, "fragment", as applied to a protein, means at least about 10 amino acids, usually about 20 contiguous amino acids, preferably at least 40 contiguous amino acids, more preferably at least 50 amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

As used herein, "test cell" means a cell that expresses a PRE1 gene in the absence of a PRE1 gene repressor. Preferably, the PRE1 gene in the test cell is under the control of a promoter that is naturally associated with a PRE1 gene.

As used herein, "vector" means a replicable nucleic acid construct, e.g., a plasmid or viral nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWING

FIG. 1 is the nucleotide sequence of a murine PRE1 cDNA, and the deduced amino acid sequence.

DETAILED DESCRIPTION

PRE1 Structure and Function

A full-length murine PRE1 cDNA has been cloned and sequenced. The PRE1 cDNA clone contains 3018 bp (FIG. 1) and includes a complete open reading frame that encodes a protein 413 amino acids in length. The sequence of the 3018 bp cDNA is shown in FIG. 1. The cDNA sequence around the first ATG matches the Kozak consensus sequence for a translational start site. The open reading frame from this methionine includes 413 amino acids, yielding a highly basic polypeptide (PI=9.41) with a predicted molecular weight of 46.4 KD. One structural feature of PRE1 is the presence of a cysteine-histidine rich segment (a.a. 118–165, H—$X_{13}$—C—$X_2$—C—$X_{10}$—C—$X_2$—C—$X_4$—H—$X_2$—C—$X_7$—C) typical of a diacylglycerol/phorbol ester (DAG_PE) binding site (Ono et al.,1989, *Proc. Natl. Acad. Sci,* 86:4868–4871). PRE1's carboxyterminal region shares some homology to the putative Ras-binding domains of other proteins (Ponting et al., 1996, *Trends In Biochem. Sci.* 21:422–425). PRE1 also has a proline rich region in its aminoterminal region, with five PXXP sequences (aa 17–20 PEPP; 31–34 PPPP; 34–37 PARP; 77–80 PVRP and 105–108 PQDP), which are possible SH3 domain binding sites (Ren et al., 1993, *Science* 259:1157–1161).

Ras interacts with downstream effectors to cause changes in cellular function, growth, and division. Mutations in this signaling pathway can lead to abnormal cell proliferation or neoplasia. Substances that block the Ras-effector interaction can thus inhibit abnormal cell proliferation or neoplasia. Screening for substances that modulate Ras-PRE1 interaction is therefore useful for identifying potential cancer therapy agents.

PRE1 may be a catalytic signaling molecule. Preliminary experiments, however, indicate that prokaryotic recombinant PRE1 (a.a. 188–413) does not alter Ras-GTP exchange or Ras-GTPase activity in vitro. PRE1 may also be an adapter molecule, serving to link activated Ras with another, presumably catalytic, signaling molecule. The Ras binding domain (a.a. 266–360) in PRE1 is located in its carboxyterminal region, and there are potential SH3 binding sites in the aminoterminal region. PRE1 may link a SH3 domain-containing protein to activated Ras. PRE1 also contains a DAG_PE binding consensus sequence motif also found in a variety of proteins involved in intracellular signaling including Raf (Rapp et al., 1988, *Cold Spring Harb. Symp. Quant. Biol.,* 53 Pt.1:173–184), PKC (Ono et al., 1989, *Proc. Natl. Acad. Sci.,* 86:4868–4871), VAV (Ahmed et al., 1992, *Biochem. J.,* 287:995–999), n-chimerin (Ahmed et al., 1990, *Biochem. J.,* 272:767–773) and DAG kinases (Sakane et al., 1990, *Nature,* 344:345–348). DAG may bind to the DAG_PE site in PRE1 and regulate its function.

Expression Control Sequences and Vectors

The PRE1 protein-encoding DNA ("PRE1 DNA") of this invention can be used in a screening method to identify a substance that inhibits cell proliferation or neoplasia in a mammal. For such uses, the PRE1 DNA is typically cloned into an expression vector, i.e., a vector wherein PRE1 DNA is operably linked to expression control sequences. The need for, and identity of, expression control sequences will vary according to the type of cell in which the PRE1 DNA is to be expressed. Generally, expression control sequences include a transcriptional promoter, enhancer, suitable mRNA ribosomal binding sites, and sequences that terminate transcription and translation. Suitable expression control sequences can be selected by one of ordinary skill in the art. Standard methods can be used by the skilled person to construct expression vectors. See generally, Sambrook et al., 1989, *Molecular Cloning: A Laboratory Manual* (2nd Edition), Cold Spring Harbor Press, Cold Spring Harbor, N.Y. Vectors useful in this invention include plasmid vectors and viral vectors. Preferred viral vectors are those derived from retroviruses, adenovirus, adeno-associated virus, SV40 virus, or herpes viruses.

PRE1 DNA In Vitro

In some embodiments of the invention, PRE1 DNA is introduced into, and expressed in, a prokaryotic cell, e.g., *Escherichia coli.* For expression in a prokaryotic cell, PRE1 DNA can be integrated into a bacterial chromosome or expressed from an extrachromosomal DNA.

In other embodiments of the invention, the PRE1 DNA is introduced into, and expressed in, a eukaryotic cell in vitro. Eukaryotic cells useful for expressing PRE1 DNA in vitro include, but are not limited to, COS, CHO, and Sf9 cells. Transfection of the eukaryotic cell can be transient or stable. The PRE1 DNA can be, but is not necessarily, integrated into a chromosome of the eukaryotic cell.

PRE1-Specific Antibody

Some embodiments of this invention include a PRE1-specific antibody. Standard protocols for monoclonal and polyclonal antibody production are known and can be carried out by one of ordinary skill in the art to obtain antibodies useful in this invention.

The invention encompasses not only an intact monoclonal or polyclonal antibody, but also an immunologically active antibody fragment. Examples of such a fragment include a Fab or F(ab$_2$) fragment, an engineered single chain Fv molecule, and a chimeric antibody. Typically, a chimeric antibody includes a variable region of a non-human antibody, e.g., a murine variable region, and a constant region of a human antibody.

Antibody Label

In some embodiments of the invention, the PRE1-specific antibody includes a detectable label. Various types of detectable labels can be linked to, or incorporated into, an antibody of this invention. Examples of useful label types include radioactive, non-radioactive isotopic, fluorescent, chemiluminescent, paramagnetic, enzyme, or colorimetric.

Examples of useful enzyme labels include malate hydrogenase, staphylococcal dehydrogenase, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, and glucoamylase, acetylcholinesterase. Examples of useful radioisotopic labels include $^3$H, $^{131}$I, $^{125}$I, $^{32}$P, $^{35}$S, and $^{14}$C. Examples of useful fluorescent labels include fluorescein, rhodamine, phycoerythrin, phycocyanin, allophycocyanin, and fluorescamine. Examples of useful chemiluminescent label types include luminal, isoluminal, aromatic acridinium ester, imidazole, acridinium salt, oxalate ester, luciferin, luciferase, and aequorin.

Suitable labels can be coupled to, or incorporated into antibodies or antibody fragments through standard techniques known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Useful chemical coupling methods include those that use glutaraldehyde, periodate, dimaleimide and m-maleimido-benzyl-N-hydroxy-succinimide ester.

Screening assays

The invention can be used to screen candidate substances for the ability to inhibit the interaction of Ras with PRE1.

In an exemplary screening method, the two-hybrid expression system described below is used to screen for substances capable of inhibiting Ras-PRE1 interaction in vivo. The two-hybrid method is a well known yeast-based genetic assay to detect protein-protein interactions in vivo (See, e.g., Bartel et al., 1993, *In Cellular Interactions in Development: A Practical Approach,* Oxford University Press, Oxford, pp. 153–179; Chien et al., 1991, *Proc. Natl. Acad. Sci. USA,* 88:9578–9582; Fields et al., 1989, *Nature,* 340:245–247; Fritz et al., 1992, *Curr. Biol.,* 2:403–405; Guarente, L., 1993, *Proc. Natl. Acad. Sci. USA,* 90:1639–1641). In this system, a GAL4 binding site, linked to a reporter gene such as lacZ, is contacted in the presence and absence of a candidate substance with a GAL4 binding domain linked to a PRE1 fragment and a GAL4 transactivation domain II linked to a Ras fragment. Expression of the reporter gene is monitored, and a decrease in its expression is an indication that the candidate substance inhibits the interaction of Ras with PRE1. One of ordinary skill in the art will recognize that other screening assays are known and can be used to identify candidate substances that inhibit Ras-PRE1 interaction.

In another screening method, one of the protein components of the Ras-PRE1 binding complex, such as Ras or a PRE1-binding fragment of Ras or PRE-1 or a Ras-binding fragment of PRE-1, is immobilized. Polypeptides can be immobilized using methods known in the art. Such methods include adsorption onto a plastic microtiter plate or specific binding of a glutathione-S-transferase (GST)-fusion protein to a polymeric bead containing glutathione. For example, GST-PRE1 (a.a. 188–413) can be bound to glutathione-Sepharose™ beads. The immobilized protein (e.g., PRE1 ) is then contacted with the labeled protein to which it binds (Ras in this example) in the presence and absence of a candidate substance. Unbound protein can be removed by washing. The complex then can be solubilized and analyzed to determine the amount of bound (labeled) protein. A decrease in binding is an indication that the candidate substance inhibits the interaction of Ras and PRE1.

A variation of the above-described screening method can be used to screen for other classes of candidate substances, e.g., those that disrupt previously-formed Ras-PRE1 complexes. In this variation, a complex containing Ras (or a PRE1-binding Ras fragment) bound to PRE1 (or a Ras-binding fragment) is immobilized and contacted with a candidate compound. Detection of disruption of the Ras-PRE1 complex by the candidate substance identifies the candidate substance as a potential modulator of Ras-mediated cellular events.

The present invention is further illustrated by the following specific examples. The examples are provided for illustration only and are not to be construed as limiting the scope or content of the invention in any way.

EXAMPLES

Cloning of PRE1 cDNA

A yeast two hybrid screen was carried out to identify potential new Ras effectors in mammalian cells. A cDNA encoding V12-H-Ras without the last four amino acids was subcloned into vector pAS-CYH-II carboxyterminal to the Gal-4 DNA binding domain. This formed the bait construct pAS-Ras, which was used to transform the yeast strain Y190. Stable transformants were selected on Trp(–) plates and a single yeast colony was picked, grown up in Trp medium and saved.

After verifying that V12-H-Ras was correctly expressed in this yeast clone, 100 μg of cDNA made from an activated mouse T cell library constructed in the GAL-4 DNA activation domain vector pACT was transformed into one million yeast cells expressing pAS-Ras. The transformants were plated out on 10 large His(-)Leu(-)Trp(-) selection plates. After eight days, 20 large colonies appeared. An X-gal filter assay was performed for all the colonies and all showed strong blue color, indicative of lacZ activity. The colonies were individually picked. Yeast plasmid DNA was isolated from each picked colony and transformed into bacterial strain WA921 by electroporation. Transformants were subjected to selection on on Leu(-) LB plus ampicillin plates. The bait plasmid pAS-Ras was usually removed by this selection, and the pACT-cDNA plasmids were isolated from the bacteria using conventional methods. Of the positive clones, two encoded a 2.5 Kb cDNA representing a new gene, which was designated PRE1.

The 2.5 Kb cDNA encoding PRE1 from the initial two-hybrid screen was isolated, labeled with $[\alpha-^{32}P]$ dCTP and used to screen cDNA libraries from mouse brain (Clontech's mouse brain 5'-stretch plus cDNA library in λ-gt 10 vector, CAT. #ML 3000a). A positive clone containing a 3018 bp insert was isolated.

By low stringency screening of cDNA libraries, at least two more cDNAs encoding polypeptides with regions similar or identical to regions of PRE1 were obtained. They diverged substantially from PRE1 in sequences aminoterminal to the Cys-His rich segment. These may represent alternative splice variants of PRE1 gene products or genes related to PRE1.

PRE1-Specific Antibody

A polyclonal antiserum was raised against a carboxyterminal fragment of PRE1 (a.a. 188–413) using conventional methods. A polyclonal antibody preparation was produced by affinity chromatography using the recombinant antigen. AGST-PRE1 (a.a. 188–213) fusion protein was used to immunize NZW rabbits. The antiserum was first depleted of GST-reacting antibodies by repeated incubation with immobilized GST. The GST depleted antiserum was then affinity purified using immobilized PRE1 (a.a. 188–413) on PVDF membrane.

Northern blot

PRE1 mRNA abundance and complexity in murine tissues was examined by Northern blot. A 210 bp PRE1 cDNA fragment (nt. 90–310) was labelled with $^{32}$P-dCTP by the random priming method and used for probing PRE1 mRNA. The mouse multiple tissue blot was purchased from Clontech and hybridized in Stratagene's quick hybridization buffer and washed according to the manufacturer's protocol. A single MRNA containing about 3.1 Kb was detected in most mouse tissues, including: heart, brain, spleen, lung, liver, skeletal muscle, kidney, and testis. Some mRNA size variation was noted. The highest levels were observed in brain, liver and spleen, with barely detectable levels in heart.

Tissue and cell line western blot

Western blots using polyclonal anti-PRE1 (a.a. 188–413) antibody were performed. Sprague-Dawley rats (65 g) were starved overnight and anesthetized with pentobarbital. Tissues from the rats were excised in the following order: gastrocnemius, testis, spleen, kidney, liver, lung and heart. Brain was excised from other intact anesthetized animals after decapitation. Cell lines were grown to 80%–90% confluency before harvesting. Both tissues and cell lines were disrupted and extracted in RIPA buffer.

An immunoblot of extracts prepared from different rat tissue was performed. A single immunoreactive band at 46 KD was seen in a brain extract. This was in agreement with the predicted size of the polypeptide encoded by PRE1 cDNA isolated from the mouse brain library. A similar 46 KD band was also seen in other tissues including lung and testis. In addition, however, prominent immunoreactivity to bands at other molecular weights was seen in most tissues, and some tissues lacked a 46 KD band entirely (e.g., skeletal muscle, heart, spleen and liver). All tissues except brain, showed a major 65 KD band, and two bands around 55 KD were also seen in lung, spleen, testis and liver. The 65 and 55 KD bands may represent isoforms of PRE1, the existence of which is suggested by the partial cDNAs isolated from a variety of cDNA libraries. The anti-PRE1 antibody also immunoblotted a single polypeptide in an extract prepared from C. elegans. This band was approximately 74 KD.

The murine brain PRE1 cDNA was tagged at the PRE1 amino terminus with an hemagglutinin (HA) epitope and expressed transiently in COS cells. In an immunoblot with anti-PRE1 antibodies, HA-PRE1 showed the expected size of 46 KD. Extracts prepared from several cell line were subjected to PRE1 immunoblot. Of the cell lines examined, only BC3H1, a vascular smooth muscle-like line derived from a radiation induced murine brain tumor, showed a single band at 46 KD. A band of similar size was seen in several other cell lines including RIE-1 (rat intestinal epithelial), MCF-7 (human breast cancer), HEK 293 (human embryonic kidney) and KB (human oral carcinoma). Immunoreactive polypeptides of 55 KD (RIE-1, MCF-7, HEK 293 and KB) and 65 KD (RIE-1, HEK 293 and KB), were at least as abundant in these cell lines, and some lines showed only bands other than the 46 KD polypeptide (e.g., Huh-7, 40 KD; L6, 55 KD).

Ras/PRE binding in vitro

A GST-PRE1 (a.a. 188–413) fusion protein (corresponding to the PRE1 polypeptide encoded by the initial cDNA isolate) was expressed and purified from E. coli. Purified, prokaryotic recombinant [c-H-Ras] (2.5 mg/ml) was loaded with [GTP-γ-S] (2 mM) or [GDP-β-S] (2 mM) at 37° C. for 15 minutes in the buffer containing 50 mM Tris-HCl, pH 7.5, 7.5 mM EDTA, 2.5 mM MgCl$_2$, 0.5 mg/ml bovine serum albumin and 1 mM DTT. Various amounts of GTP-γ-S or GDP-β-S loaded Ras proteins were mixed with purified prokaryotic recombinant GST-PRE (188–413) or GST as a control. After incubation at 30° C. for 20 minutes, 0.4 ml of 7.5% (V/V) glutathione-Sepharose ™ beads suspended in the binding buffer (50 mM Tris-HCl, pH 7.5, 150 mM NaCl, 1% Triton X-100, 0.2% BSA and 2 mM DTT), was added to recover GST or GST fusion proteins and any associated proteins. After tumbling at 4° C. for 30 minutes, the beads were washed five times with the binding buffer and the bound polypeptides were eluted with SDS sample buffer.

The proteins were separated by SDS-PAGE, transferred to PVDF membrane and probed with the monoclonal anti-Ras Pan-Ras-2 antibodies (Oncogene Science). The bands were visualized using the ECL reagents (Amersham). This assay showed that GST-PRE1 (a.a. 188–413), but not GST, binds to Ras, and considerably more Ras-GTP-γ-S bound than Ras-GDP-β-S. These results showed the direct binding of PRE1 and Ras proteins, and established the binding of the two proteins was GTP-dependent.

Ras-PRE1 association in COS-7 cells

The following experiment was carried out using the COS-7 transient expression system. This system was used because it was previously shown that in serum-starved COS-7 cells, Ras is mostly in the GDP bound form, and addition of epidermal growth factor (EGF) or tetradecanoyl phorbol acetate (TPA) rapidly increases Ras-GTP charging (McCollam et al., 1997, *J. Biol. Chem.*, 270:15954–15947).

COS-7 cells were plated at a density of 1.2 million per 10 cm dish and transfected 24 hours later with 7 μg of pMT2-HA-c-H-Ras (Sambrook et al., 1989, *Molecular Cloning: A Laboratory Manual,* (2nd Edition), Cold Spring Harbor Press, Cold Spring Harbor, N.Y.) or empty vector and 12 μg of pEBG-GST-PRE1 (Nagata et al., 1990, *Nucleic Acids Research,* 18:5322) using the DEAE-Dextran method. Forty-eight hours later, cells were starved for 24 hours and subsequently were stimulated with of EGF (100 ng/ml) or TPA (0.1 μM) for various times. Cells were extracted in lysis buffer (30 mM HEPES, pH 7.4, 1% Triton X-100, 20 mM β-glycerophosphate, 2 mM NaPP$_i$, 1 mM orthovanadate, 20 mM NaF, 20 mM KCl, 2 mM EGTA, 3 mM EDTA, 7.5 mM MgCl$_2$, 14 mM β-ME and a cocktail of protease inhibitors). Lysates were freeze-thawed once and spun at 17000×g for 20 minutes. Supernatants were incubated with monoclonal anti-HA antibodies (12CA5) and protein A-G Sepharose™ beads for 3–4 hours at 4° C. and then washed extensively with lysis buffer. The washed beads were eluted in SDS sample buffer. The extracted proteins were subjected to SDS-PAGE, transferred on PVDF membranes and probed using affinity-purified anti-GST polyclonal antibodies or monoclonal anti-HA antibodies. Bound antibodies were visualized using ECL. This assay showed that GST-PRE1 was specifically bound by HA-c-H-Ras, but only after the cells were treated with EGF or TPA. The expression of HA-c-H-Ras and of GST-PRE1 was uniform throughout. Thus, PRE1 was not detectably associated with Ras in serum-starved COS cells, however, within 5 minutes after stimulation by EGF (or TPA), PRE1 associated specifically with Ras. This association diminished by 15 minutes after EGF addition, and was largely reversed by 40 minutes. This may have reflected the downregulation of Ras activation after EGF treatment.

Ras-PRE association in KB cells

In situ association between endogenous Ras and endogenous PRE1, under conditions where the levels of the two polypeptides were not increased artificially by transient overexpression, was examined. The human oral carcinoma cell line, KB, expressed both a readily detectable level of PRE1 as well as a substantial number of EGF receptors. KB cells were grown to 80% confluency, starved of serum for 24 hours and subsequently stimulated with EGF (100 ng/ml) for various times. Triton X-100 soluble cell lysates were subjected to immunoprecipitation using the monoclonal anti-Ras antibody, Y13-238, which is known to enable isolation of Ras-effector complexes. The Ras immunoprecipitates were washed extensively with the lysis buffer, eluted in SDS sample buffer and subjected to SDS-PAGE, transferred to PVDF membrane and immunoblotted with the affinity purified polyclonal anti-PRE1 antibodies. These experiments showed that, although equal amounts of endogenous Ras was recovered in all samples, the Ras immunoprecipitates contain immunoreactive PRE1 only after treatment of the cells with EGF. The time course of Ras-PRE1 association after EGF treatment in KB cells was more sustained than that observed in COS-7 cells. This may have reflected a different time course of downregulation of Ras activation in those cells. The 46 KD immunoreactive PRE1 polypeptide was recovered with c-Ras, but not the equally abundant 55 KD protein.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3018 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 31...1269

(xi) SEQUENCE DESCRIPTION: SEQ ID NO:1:

```
GTAGCTGCGC CGCTGACTGA GGCCTTGGCC  ATG GCT TCC CCG GCC ATC GGG CAA      54
                                 Met Ala Ser Pro Ala Ile Gly Gln
                                  1               5
```

```
CGT CCC TAC CCG CTG CTC CTA GAT CCC GAG CCG CCG CGG TAT CTG CAG        102
Arg Pro Tyr Pro Leu Leu Leu Asp Pro Glu Pro Pro Arg Tyr Leu Gln
     10              15                  20

AGT CTG GGT GGC ACC GAG CCG CCA CCT CCC GCC CGG CCG CGC CGC TGC        150
Ser Leu Gly Gly Thr Glu Pro Pro Pro Pro Ala Arg Pro Arg Arg Cys
 25              30                  35                  40

ATC CCC ACG GCC CTG ATC CCC GCG GCC GGG GCG TCA GAG GAT CGC GGT        198
Ile Pro Thr Ala Leu Ile Pro Ala Ala Gly Ala Ser Glu Asp Arg Gly
                 45                  50                  55

GGC AGG AGG AGT GGC CGG AGG GAC CCC GAA CCC ACG CCC CGA GAC TGC        246
Gly Arg Arg Ser Gly Arg Arg Asp Pro Glu Pro Thr Pro Arg Asp Cys
             60                  65                  70

CGA CAC GCT CGC CCT GTC CGG CCC GGT CTG CAG CCG AGA CTG CGG CTG        294
Arg His Ala Arg Pro Val Arg Pro Gly Leu Gln Pro Arg Leu Arg Leu
             75                  80                  85

CGA CCT GGG TCA CAC CGA CCC CGC GAC GTG AGG AGC ATC TTC GAG CAG        342
Arg Pro Gly Ser His Arg Pro Arg Asp Val Arg Ser Ile Phe Glu Gln
         90                  95                 100

CCG CAG GAT CCC CGC GTC TTG GCC GAG AGA GGC GAG GGG CAC CGT TTC        390
Pro Gln Asp Pro Arg Val Leu Ala Glu Arg Gly Glu Gly His Arg Phe
105             110                 115                 120

GTG GAA CTG GCG CTG CGG GGC GGT CCG GGC TGG TGT GAC CTG TGC GGA        438
Val Glu Leu Ala Leu Arg Gly Gly Pro Gly Trp Cys Asp Leu Cys Gly
                125                 130                 135

CGA GAG GTG CTG CGG CAG GCG CTG CGC TGC GCT AAT TGT AAA TTC ACC        486
Arg Glu Val Leu Arg Gln Ala Leu Arg Cys Ala Asn Cys Lys Phe Thr
            140                 145                 150

TGC CAC TCG GAG TGC CGC AGC CTG ATC CAG TTG GAC TGC AGA CAG AAG        534
Cys His Ser Glu Cys Arg Ser Leu Ile Gln Leu Asp Cys Arg Gln Lys
            155                 160                 165

GGG GGC CCT GCC CTG GAT AGA CGC TCT CCA GGA AGC ACC CTC ACC CCA        582
Gly Gly Pro Ala Leu Asp Arg Arg Ser Pro Gly Ser Thr Leu Thr Pro
170                 175                 180

ACC TTG AAC CAG AAT GTC TGT AAG GCA GTG GAG GAG ACA CAG CAC CCG        630
Thr Leu Asn Gln Asn Val Cys Lys Ala Val Glu Glu Thr Gln His Pro
185                 190                 195                 200

CCC ACG ATA CAG GAG ATC AAG CAG AAG ATT GAC AGC TAT AAC AGC AGG        678
Pro Thr Ile Gln Glu Ile Lys Gln Lys Ile Asp Ser Tyr Asn Ser Arg
                205                 210                 215

GAG AAG CAC TGC CTG GGC ATG AAG CTG AGT GAA GAT GGC ACC TAC ACA        726
Glu Lys His Cys Leu Gly Met Lys Leu Ser Glu Asp Gly Thr Tyr Thr
            220                 225                 230

GGT TTC ATC AAA GTG CAT TTG AAG CTC CGA CGG CCA GTG ACG GTG CCC        774
Gly Phe Ile Lys Val His Leu Lys Leu Arg Arg Pro Val Thr Val Pro
            235                 240                 245

GCT GGA TCC GGC CCC AGT CCA TCT ATG GAT GCC ATT AAG GAA GTG AAC        822
Ala Gly Ser Gly Pro Ser Pro Ser Met Asp Ala Ile Lys Glu Val Asn
250                 255                 260

CCT GCA GCC ACC ACA GAC AAG CGG ACT TCC TTC TAC CTG CCA CTC GAT        870
Pro Ala Ala Thr Thr Asp Lys Arg Thr Ser Phe Tyr Leu Pro Leu Asp
265                 270                 275                 280

GCC ATC AAG CAG CTA CAT ATC AGC AGC ACC ACC ACG GTT AGT GAG GTC        918
Ala Ile Lys Gln Leu His Ile Ser Ser Thr Thr Thr Val Ser Glu Val
                285                 290                 295

ATC CAG GGG CTG CTC AAG AAG TTC ATG GTT GTG GAC AAC CCA CAG AAG        966
Ile Gln Gly Leu Leu Lys Lys Phe Met Val Val Asp Asn Pro Gln Lys
            300                 305                 310

TTT GCA CTT TTT AAG CGG ATA CAC AAA GAT GGA CAA GTG CTC TTC CAG       1014
Phe Ala Leu Phe Lys Arg Ile His Lys Asp Gly Gln Val Leu Phe Gln
```

```
                    315                 320                 325
AAA CTC TCC ATT GCT GAC TAT CCT CTC TAC CTT CGT CTG CTC GCT GGG            1062
Lys Leu Ser Ile Ala Asp Tyr Pro Leu Tyr Leu Arg Leu Leu Ala Gly
            330                 335                 340

CCT GAC ACC GAT GTT CTC AGC TTT GTG CTA AAG GAG AAT GAA ACT GGA            1110
Pro Asp Thr Asp Val Leu Ser Phe Val Leu Lys Glu Asn Glu Thr Gly
345                 350                 355                 360

GAG GTG GAG TGG GAT GCC TTT TCC ATT CCT GAA CTC CAG AAC TTT TTA            1158
Glu Val Glu Trp Asp Ala Phe Ser Ile Pro Glu Leu Gln Asn Phe Leu
                365                 370                 375

ACT ATC CTG GAA AAA GAG GAG CAG GAC AAG ATC CAT CAA CTG CAA AAG            1206
Thr Ile Leu Glu Lys Glu Glu Gln Asp Lys Ile His Gln Leu Gln Lys
            380                 385                 390

AAG TAC AAC AAA TTC CGT CAG AAA CTG GAA GAG GCA TTA CGA GAG TCC            1254
Lys Tyr Asn Lys Phe Arg Gln Lys Leu Glu Glu Ala Leu Arg Glu Ser
            395                 400                 405

CAA GGG AAG CCG GGG TAACCAGCCG ACTTCCTGTC CTCTCAGTGC CCTCCAATTT            1309
Gln Gly Lys Pro Gly
        410

ATTTTATTGT TAATTATTTT GCAACAAAGA GTTACTGTTA AGACACCTCT GGTGGTTCCA          1369

CCAGTCGCCT GCCCAGCAGT TAACAGATGT GGCACAAAGT CTCTTCCACG CAGTGTCTAT          1429

GCAGGGTTCC GATTCCTGCT AACCCACCAC ACCATGGCTC TGGAGAGCTT CCCGCCTGGG          1489

ATCAGAACTC CTGTGGAATG ACCAGTGTTT CCCTGCTCAG TCTGCTGGCC TCTCAGAAAC          1549

CAAATAGTTG CCTCTCTGGT CACCAAACTC CAATCAATCA CCAGCCGGCA AAAGGAAAGA          1609

AAGGTTTCAG AGCCTGTGTG TTCTTTCTCT GGATTTACTC TTCAGTTCCT CTTTTGGTTT          1669

GTTTGGTTGG TTTTTTTTGG CCACGTATAG TATATTTAAG GATCAAATGT GGCATATTCA          1729

TTCTAGCTAA GTCCTTGAAA GCAGGAAAAT GCTCATGAAA GGACTGTCCT TGCCCCAAGG          1789

TGCCTCTTCT TCTCTAGTAC TAGACACTCA GGGTCAGCCT GAGATTTCAA GAGGCTACAG          1849

CCTGACCAGG CCGTCTTCTT ATTACCCAGC AGGCTGTGTG CATGCAAACC CAAAGACATA          1909

TATGCACATC TGTGTGGTAT TTCAGCATGT CTCTGTCCAA TGTTTGATAT GTTAACATTT          1969

GAATTTAATG CTGTCCTCCT TATGGGTTTC TACCAAAGAG AAACCAGCCA CTTATCAATT          2029

TTAGTTTCTT GCTGAGCTGC CAGAAAGTAT TACAGAGAAG CACATCCAAG CTGTCTGTGG          2089

CCTACGCCTG CAGGGGGTGG GGGGCCTGAA TCTCCTTGGC CTTCAGTTCC ACCTCCACCT          2149

CTGGCTTTAG GGTCTCCAGC TGTTGCCTGA GTAGTAGCTT TGATTACAGC GGTAAAGTCC          2209

TCCAACTTGG AGTCCTTTCT GGTGGGAAGC ATGGTCTGCT CGCAGCACAG CACTGAGCAG          2269

ACCCGTGGGC CTGACTTCCC TGGTGACTTC AGTGCCTTTT TGTTTGCAGA GAAAAGAGTG          2329

GGGCACTTTG CTTGAAGCTC TCTGCTGGCT TGCCCCTGGC AGGAAGTGGA CAATGGTGCT          2389

ATAGAGCCAA GGACACAGCC TCAGAGCACA GGGTGATTGA TGATCAGCCT CTTTCCCATC          2449

AAGCTTCCCG GTCAGGCTTT GACTTTGAAG ATGCGAGGTT ACTAGACTGC ATTGACAGCA          2509

TCAGATTATG ACTCCAACTC TTGAGTAGTT CAGACTTAAA ACCAATCAGC CAGAGTAGCC          2569

AGGACTGCAA AGACACTCAA TACAGATGGA GAAAAACTTG TCCCTTTAAA AGAGGGCCAG          2629

TGTTTCAATT GAGCCTCCAG AGGAGACCAC TTTCATGTTG TGCTTGCCTT TCCATACCCT          2689

TTCCTCGGGT TGTTTTAAGC CCAAGCTTCT CCGTGTAGCC TAAAAAGTTC CCTACCAGCC          2749

CAGCTGAAGC CACACTGCTC CCGTCCCAGA AGAACGCCAA ATCCTTGTCA TTCAAACTGT          2809

GCATCGTTTG CAGAGCTGCA AAAAGCAACA TGAGCTAGCG ACTCTGAGGT TGTGCACGCC          2869

ATCAGCCCCT TGGCTGCCTG AGGTCTCATG CCCAGCCTTA CACCTCTCTC CCTTAAGAAG          2929
```

```
CCCCCGTCCT GCTGTGTACT ACAGGGGCAC GTGGAATCAT TCCCTTCATC CTGCATGTCT    2989

GTAGCGTTAG GAGAAGGCAT GGCTCCTGC                                      3018
```

(2) INFORMATION FOR SEQ ID NO:2:

(i) SEQUENCE CHARACTERISTICS:
        (A) LENGTH: 413 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

```
Met Ala Ser Pro Ala Ile Gly Gln Arg Pro Tyr Pro Leu Leu Leu Asp
  1               5                  10                  15

Pro Glu Pro Pro Arg Tyr Leu Gln Ser Leu Gly Thr Glu Pro Pro
             20                  25                  30

Pro Pro Ala Arg Pro Arg Arg Cys Ile Pro Thr Ala Leu Ile Pro Ala
             35                  40                  45

Ala Gly Ala Ser Glu Asp Arg Gly Gly Arg Arg Ser Gly Arg Arg Asp
     50                  55                  60

Pro Glu Pro Thr Pro Arg Asp Cys Arg His Ala Arg Pro Val Arg Pro
 65              70                  75                      80

Gly Leu Gln Pro Arg Leu Arg Leu Arg Pro Gly Ser His Arg Pro Arg
                 85                  90                  95

Asp Val Arg Ser Ile Phe Glu Gln Pro Gln Asp Pro Arg Val Leu Ala
                100                 105                 110

Glu Arg Gly Glu Gly His Arg Phe Val Glu Leu Ala Leu Arg Gly Gly
            115                 120                 125

Pro Gly Trp Cys Asp Leu Cys Gly Arg Glu Val Leu Arg Gln Ala Leu
        130                 135                 140

Arg Cys Ala Asn Cys Lys Phe Thr Cys His Ser Glu Cys Arg Ser Leu
145                 150                 155                 160

Ile Gln Leu Asp Cys Arg Gln Lys Gly Gly Pro Ala Leu Asp Arg Arg
                165                 170                 175

Ser Pro Gly Ser Thr Leu Thr Pro Thr Leu Asn Gln Asn Val Cys Lys
            180                 185                 190

Ala Val Glu Glu Thr Gln His Pro Pro Thr Ile Gln Glu Ile Lys Gln
        195                 200                 205

Lys Ile Asp Ser Tyr Asn Ser Arg Glu Lys His Cys Leu Gly Met Lys
    210                 215                 220

Leu Ser Glu Asp Gly Thr Tyr Thr Gly Phe Ile Lys Val His Leu Lys
225                 230                 235                 240

Leu Arg Arg Pro Val Thr Val Pro Ala Gly Ser Gly Pro Ser Pro Ser
                245                 250                 255

Met Asp Ala Ile Lys Glu Val Asn Pro Ala Ala Thr Thr Asp Lys Arg
            260                 265                 270

Thr Ser Phe Tyr Leu Pro Leu Asp Ala Ile Lys Gln Leu His Ile Ser
        275                 280                 285

Ser Thr Thr Thr Val Ser Glu Val Ile Gln Gly Leu Leu Lys Lys Phe
    290                 295                 300

Met Val Val Asp Asn Pro Gln Lys Phe Ala Leu Phe Lys Arg Ile His
305                 310                 315                 320
```

-continued

```
Lys Asp Gly Gln Val Leu Phe Gln Lys Leu Ser Ile Ala Asp Tyr Pro
                325                 330                 335

Leu Tyr Leu Arg Leu Leu Ala Gly Pro Asp Thr Asp Val Leu Ser Phe
            340                 345             350

Val Leu Lys Glu Asn Glu Thr Gly Glu Val Glu Trp Asp Ala Phe Ser
        355             360                 365

Ile Pro Glu Leu Gln Asn Phe Leu Thr Ile Leu Glu Lys Glu Glu Gln
    370             375                 380

Asp Lys Ile His Gln Leu Gln Lys Lys Tyr Asn Lys Phe Arg Gln Lys
385             390             395                 400

Leu Glu Glu Ala Leu Arg Glu Ser Gln Gly Lys Pro Gly
                405             410
```

Other embodiments are within the following claims.

We claim:

1. An isolated DNA comprising a nucleotide sequence whose complement hybridizes under high stringency conditions to a DNA whose nucleotide sequence consists of SEQ ID NO:1, which isolated DNA encodes a protein that comprises a domain consisting of amino acids 266–360 of SEQ ID NO:2, or amino acids 266–360 with one or more conservative amino acid substitutions therein.

2. The DNA of claim 1, wherein said protein has an amino acid sequence consisting of SEQ ID NO:2.

3. The DNA of claim 2, wherein said nucleotide sequence is nucleotide 31 to nucleotide 1269 of SEQ ID NO:1.

4. A vector comprising the DNA of claim 1.

5. The vector of claim 4, wherein said DNA is operably linked to one or more expression control sequences.

6. A cell selected from the group consisting of a cell into which the DNA of claim 1 has been introduced, and a cell descended from a cell into which the DNA of claim 1 has been introduced.

7. An isolated DNA comprising a nucleotide sequence that encodes the amino acid sequence of SEQ ID NO:2 or an amino acid sequence with one or more conservative amino acid substitutions therein.

8. A method of producing a PRE1 protein, said method comprising the steps of:

(a) providing a cell transformed with the isolated DNA of claim 1 or 7;

(b) culturing said cell; and (c) collecting said PRE1 protein encoded by said nucleotide sequence.

* * * * *

UNITED STATES PATENT AND TRADEMARK OFFICE
CERTIFICATE OF CORRECTION

| | | |
|---|---|---|
| PATENT NO. | : 6,140,488 | Page 1 of 1 |
| APPLICATION NO. | : 08/942572 | |
| DATED | : October 31, 2000 | |
| INVENTOR(S) | : Joseph Avruch and Xian-Feng Zhang | |

It is certified that error appears in the above-identified patent and that said Letters Patent is hereby corrected as shown below:

On line 1 please insert the following paragraph:

--This invention was made with Government support under Grant No. GM051281 awarded by the National Institutes of Health. The Government has certain rights in this invention.--

Signed and Sealed this

Seventh Day of July, 2009

JOHN DOLL
*Acting Director of the United States Patent and Trademark Office*